(12) United States Patent
Strong et al.

(10) Patent No.: US 6,402,759 B1
(45) Date of Patent: Jun. 11, 2002

(54) SURGICAL FASTENER DRIVER

(75) Inventors: J. Todd Strong, Birmingham, AL (US); Rickey D. Hart, Plainville, MS (US); R. Steve Boggan, Hoover, AL (US); Prasad V. Nalluri, Jacksonville, FL (US)

(73) Assignee: Biohorizons Implant Systems, Inc., Birmingham, AL (US)

( * ) Notice: Subject to any disclaimer, the term of this patent is extended or adjusted under 35 U.S.C. 154(b) by 0 days.

(21) Appl. No.: 09/458,914

(22) Filed: Dec. 10, 1999

Related U.S. Application Data
(60) Provisional application No. 60/111,828, filed on Dec. 11, 1998.

(51) Int. Cl.[7] ............................................. A61B 17/58
(52) U.S. Cl. ........................................ 606/104; 81/463
(58) Field of Search ........................... 606/99, 100, 104; 81/44, 463; 227/175.1

(56) References Cited

U.S. PATENT DOCUMENTS

| | | | |
|---|---|---|---|
| 3,010,193 A | * | 11/1961 | Croall, Jr. et al. |
| 5,398,861 A | * | 3/1995 | Green |
| 5,741,268 A | * | 4/1998 | Schultz ..................... 606/104 |
| 5,928,244 A | * | 7/1999 | Tovey et al. ............... 606/104 |
| 6,273,893 B1 | * | 8/2001 | McAllen, III et al. ...... 606/104 |

* cited by examiner

*Primary Examiner*—Jeffrey A. Smith
(74) *Attorney, Agent, or Firm*—Needle & Rosenberg, P.C.

(57) ABSTRACT

A surgical fastener driver has a handle and a tube extending therefrom. The handle defines a cavity therein. The tube is in communication with the cavity and is affixed to the handle. The tube extends outwardly from the cavity to a seat. The cavity is shaped so as to receive a surgical fastener therein. A piston, having a outward end, is disposed within the tube and extends from the cavity to the seat. The piston has a retracted position, in which the outward end does not extend into the seat, and an extended position, in which the outward end extends into the seat. A trigger is integrated with the handle and has a first state in which the piston is held in the retracted position and a second state in which the piston is released so as to allow the piston to move to the extended position. A driver, that is disposed within the cavity, exerts outward force on the piston so as to drive the piston into the extended position when the trigger is in the second state.

8 Claims, 2 Drawing Sheets

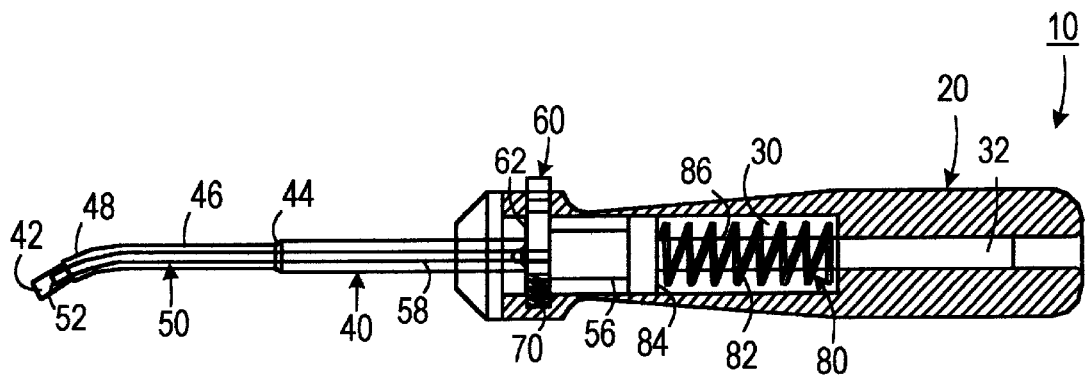
FIG. 1A
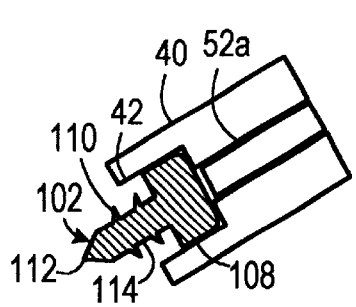 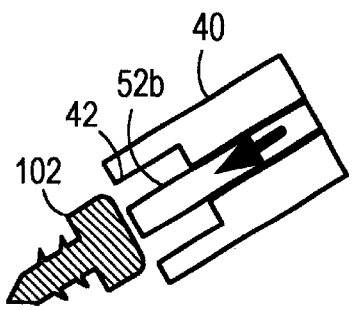 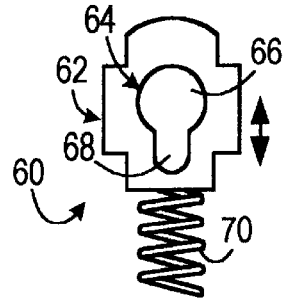
FIG. 1B   FIG. 1C   FIG. 1D
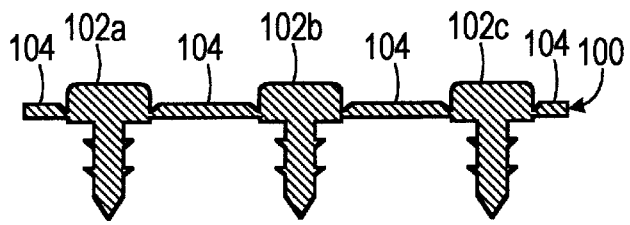
FIG. 2A
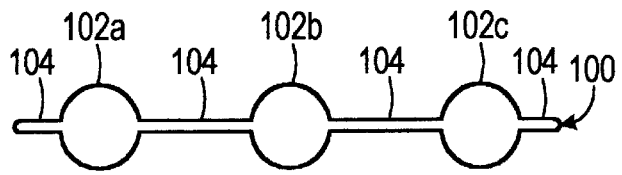
FIG. 2B

SURGICAL FASTENER DRIVER

REFERENCE TO A PROVISIONAL APPLICATION

This application for letters patent claims priority under 35 U.S.C. § 119(e) on a provisional patent application, Ser. No. 60/111,828, filed on Dec. 11, 1998.

BACKGROUND OF THE INVENTION

1. Field of the Invention

The invention relates to medical devices and, more particularly, to systems for applying surgical fasteners that secure membranes to biological tissues (such as bone).

2. Description of the Prior Art

In surgery, such as reconstructive oral surgery, when grafting bone a membrane is placed over the bone to allow the bone to regrow without contamination. The membrane is typically fastened to the bone using screws or hand-driven tacks. Because screws are small, and therefore hard to drive into bone, they currently are rarely used in oral surgery.

Hand driven tacks are more commonly used. They are held by a pick up tool and driven with a mallet. They may also be pushed in by hand. The tools employed tend to be bulky and, given that the tacks used tend to be small, the tacks are hard to handle.

Therefore, there is a need for a tissue tack system that facilitates the handling and applying of tissue tacks.

SUMMARY OF THE INVENTION

One aspect of the invention is a surgical fastener driver having a handle and a tube extending therefrom. The handle defines a cavity therein. The tube is in communication with the cavity and is affixed to the handle. The tube extends outwardly from the cavity to a seat, which is shaped so as to receive a surgical fastener therein. A piston, having a outward end, is disposed within the tube and extends from the cavity to the seat. The piston has a retracted position, in which the outward end does not extend into the seat, and an extended position, in which the outward end extends into the seat. A trigger is integrated with the handle and has a first state in which the piston is held in the retracted position and a second state in which the piston is released so as to allow the piston to move to the extended position. A driver, that is disposed within the cavity, exerts outward force on the piston so as to drive the piston into the extended position when the trigger is in the second state.

In another aspect, the invention is a surgical fastener for securing surgical membrane materials to body tissues (such as bone). The fastener includes a tack that includes a stem having a proximal end and a distal end, a head disposed at the proximal end of the stem, and a plurality of discrete axially spaced annular ribs disposed in successive longitudinal positions along the stem. The head has a diameter sized to frictionally fit within a seat of a delivery device.

In yet another aspect, the invention is a holder for surgical fasteners that includes a first block and a second block. The first block has a top surface and defines a plurality of cavities opening to the top surface, wherein each cavity is shaped so as to be capable of receiving a tack therein. The second block has an upper surface and an opposite lower surface complementary in shape to the top surface of the first block. The second block defines a plurality of holes passing from the upper surface to the lower surface. Each of the plurality of holes is in alignment with a corresponding cavity in the first block when the lower surface of the second block is placed against the top surface of the first block. A loading pin is disposed within a selected one of the plurality of cavities through at least a portion of the corresponding hole.

These and other aspects of the invention will become apparent from the following description of the preferred embodiment taken in conjunction with the following drawings, although variations and modifications may be effected without departing from the spirit and scope of the novel concepts of the disclosure.

BRIEF DESCRIPTION OF THE FIGURES OF THE DRAWINGS

FIG. 1A is a schematic diagram of an embodiment of a surgical fastener driver in accordance with the invention.

FIG. 1B is a schematic diagram of a detail of the seat in accordance with the embodiment of FIG. 1A, showing the piston in the retracted position.

FIG. 1C is a schematic diagram of a detail of the seat in accordance with the embodiment of FIG. 1A, showing the piston in the extended position.

FIG. 1D is a schematic diagram of a detail of the trigger in accordance with the embodiment of FIG. 1A.

FIG. 2A is a cross sectional view of a plurality of tacks connected by a runner.

FIG. 2B is a top plan view of the plurality of tacks of FIG. 2A.

DETAILED DESCRIPTION OF THE PREFERRED EMBODIMENTS

Figure 3A:
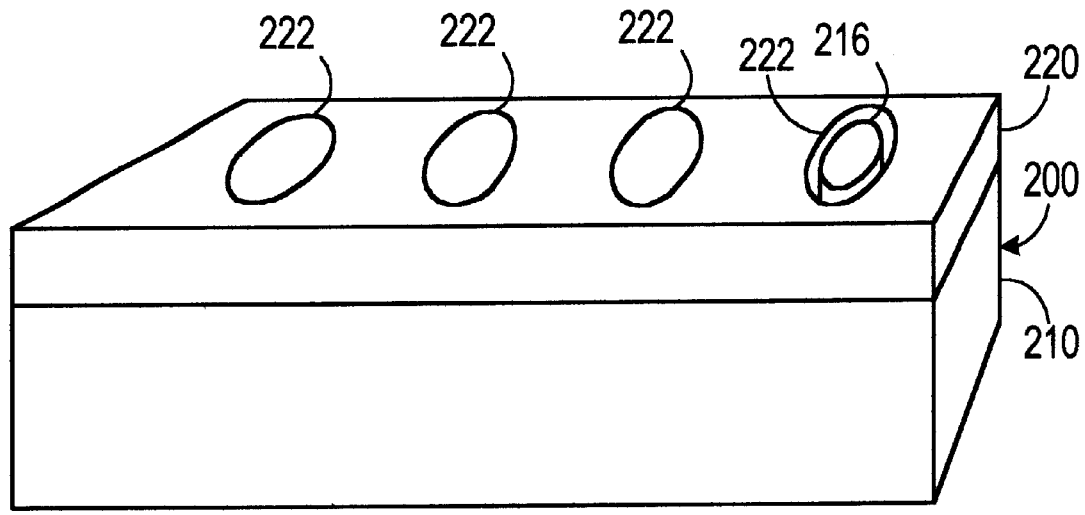
FIG. 3A is a perspective view of a holder for surgical fasteners in accordance with one embodiment of the invention.

A preferred embodiment of the invention is now described in detail. Referring to the drawings, like numbers indicate like parts throughout the views. As used in the description herein and throughout the claims that follow, "a," "an," and "the" includes plural reference unless the context clearly dictates otherwise. Also, as used in the description herein and throughout the claims that follow, the meaning of "in" includes "in" and "on" unless the context clearly dictates otherwise. Also, "complimentary in shape" means generally having compatible dimensions, without necessarily having an identical shape.

As shown in FIGS. 1A–1D, the surgical fastener driver 10, according to one illustrative embodiment of the invention, includes a handle 20 that defines a cavity 30. The cavity 30 is cylindrical and has a smaller elongated alignment cavity 32 extending therefrom. The handle 20 may be machined from metal, such as aluminum, stainless steel, or one of many metals typically used in medical instruments or from other materials generally known in the art. A tube 40 extends from the cavity 30 and is affixed to the handle 20. The hollow core of the tube 40 is in communication with the cavity 30. The tube 40 ends in a seat 42 that is shaped so as to receive a surgical fastener 102 therein. The tube 40 may be strengthened without increasing its bulk near the seat 42 by including a taper 44, thereby allowing for the use of narrower tubing near the seat 42. The tube includes a first section 46 and a second section 48. The second section 48 deflects at an angle from the first section 46 to facilitate placement of surgical fasteners in hard to reach areas.

A piston 50, having a outward end 52, is disposed within the tube 40 and extends from the cavity 30 to the seat 42. The piston 50 has a first portion 58 and a second portion 56. The cross-section of the second portion 56 is greater than the cross section of the first portion 58. As demonstrated in FIG. 1B, the piston 50 has a retracted position, in which the outward end 52a does not extend into the seat 42, so that a surgical fastener 102 may be held in the seat 42. As demonstrated in FIG. 1C, the piston 50 also has an extended position, in which the outward end 52b extends into the seat 42. When the piston 52b is forced into the extended position, the surgical fastener 102 is then forced out of the seat 42. Thus, when the seat 42 is placed against a membrane, the fastener 102 is forced into the membrane, thereby fastening it to the bone.

A trigger 60 is integrated with the handle 20. The trigger 60 has a first state in which the piston 50 is held in the retracted position and a second state in which the piston 50 is released so as to be allowed to move to the extended position. As shown in detail in FIG. 1D, The trigger 60 includes a locking member plate 62 that defines a hole 64 passing therethrough. The hole 64 includes a small portion 68 that allows the first portion 58 of the piston 50 to pass therethrough, but prevents the second portion 56 of the piston from passing therethrough. The small portion 58 thus restricts the piston 50 when the plate 62 is in a first position corresponding to the first state of the trigger 60. The hole 64 also has a large portion 66 that allows both the first portion 58 and the second portion 56 to pass therethrough when the plate 62 is in a second position corresponding to the second state of the trigger 60. The trigger 60 also includes a second spring 70 that maintains the plate 62 in the first position until it is pushed down, thereby releasing the piston 50.

A driver 80 that exerts outward force on the piston 50 is disposed within the cavity 30. The driver 80 drives the piston 50 into the extended position when the trigger 60 is in the second state. In one illustrative embodiment, the driver 80 includes a spring 82 that applies force to a plunger head 84 that caps one end of a plunger cylinder 86. The plunger head 84 has dimensions complimentary to that of the cavity 30 so as to be able to slide back and forth within the cavity 30. The plunger cylinder 86 fits within the elongated alignment cavity 32 to maintain alignment of the plunger head 84. The spring 82 applies force on the plunger head 84, which in turn applies force to the piston 50, thereby causing the piston 50 to force the fastener 102 into tissue when the trigger 60 releases the piston 50.

As shown in detail in FIG. 1B, one example of a surgical fastener 102, adapted for securing surgical membrane materials to body tissues, is a tack that includes a stem 114 having a proximal and distal end. The tack could comprise, for example, a bio-absorbable material (such as PLLA) or a medical grade metal. A head 108 is disposed at the proximal end and the distal end terminates at a point 112. A plurality of discrete axially spaced annular ribs 110 is disposed in successive longitudinal positions along the stem 114. The head 108 has a diameter sized to frictionally fit within a seat 42 of the delivery device 10.

Figure 3B:
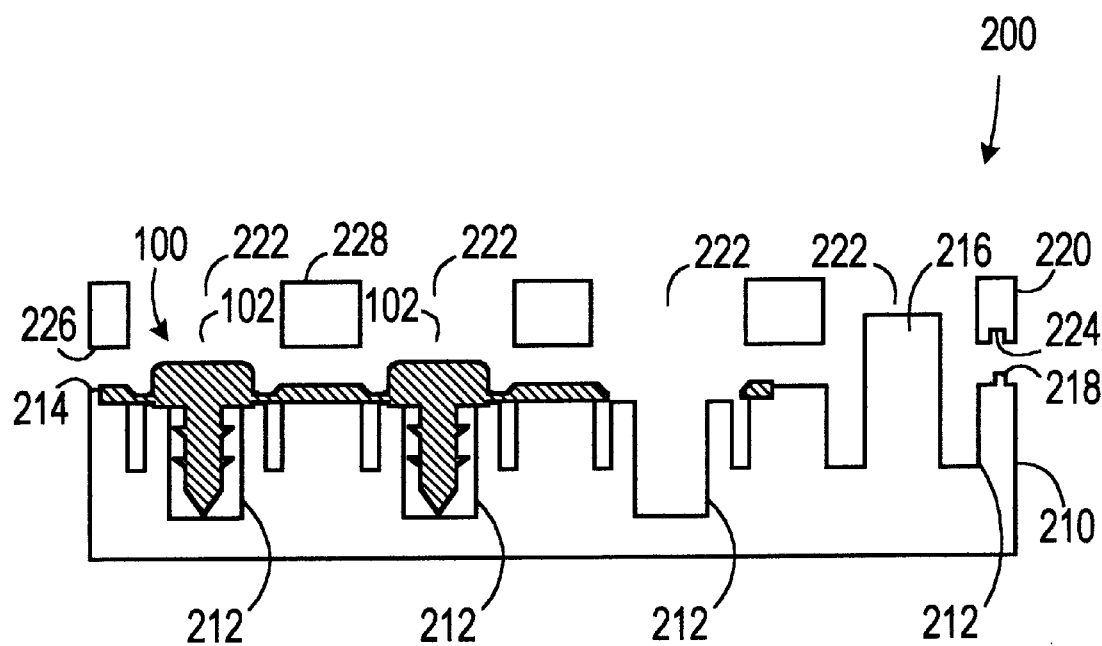
FIG. 3B is a cross sectional view of the holder shown in FIG. 3A.

As shown in FIGS. 2A and 2B, a tack strip 100 may be formed from a plurality of fasteners 102a–c connected by an integrally formed linear runner 104. Such a tack strip 100 would facilitate ease of use with a holder 200, as shown in FIGS. 3A and 3B. The holder 200 includes a first block 210 and a second block 220. The first block 210 has a top surface 214 to which a plurality of cavities 212 open. Each cavity 212 is capable of receiving a tack therein. The second block 220 has an upper surface 228 and an opposite lower surface 226 that is complementary in shape to the top surface 214 of the first block 210. The second block 220 defines a plurality of holes 222 passing therethrough so that each of the plurality of holes 222 is in alignment with a corresponding cavity 212 in the first block 210 when the lower surface 226 of the second block 220 is placed against the top surface 214 of the first block 210. A loading pin 216 is disposed within a selected one of the plurality of cavities 212 and through at least a portion of the corresponding hole 222.

If the holder 200 is to be reusable, both the first block 210 and the second block 220 should comprise a material able to withstand standard sterilization techniques (such as exposure to high temperature or radiation). For example, in one embodiment, metal is used. If the holder 200 is to be disposable, then one of many materials known to those of skill in the art could be used (e.g., polycarbonate).

To facilitate alignment and securing of the first block 210 and the second block 220, one or more pins 218 may be added to extend from the top surface 214 of the first block 210 and one or more holes 224 may be added to extend into the lower surface 226 of the second block 220. Each hole 224 is complementary in shape to, and in alignment with, a selected pin 218. As is readily understood, the pins 218 could extend from the second block 220 while the holes extend into the first block 210 without departing from the scope of the invention.

Referring to all of the figures, in using the holder 200, a tack strip 100 is placed so that the individual tacks 102 fit into the cavities 212. The second block 220 is then secured to the first block 210. The operator then uses the driver 10 by forcing the distal end 52 of the piston 50 down on to the loading pin 216. The piston 50 is forced back until the trigger 60 locks it into the retracted position. The seat 42 is then placed over one of the available tacks 102 in the holder 200 and pushed down until the tack 102 breaks away from the runner 104 and fits into the seat 42 (as shown in FIG. 1B). The seat 42 is then placed against the membrane to be fastened, the trigger plate 52 is pressed down (thereby releasing the piston 50) and the tack 102 is forced into the membrane and the into the tissue to which the membrane is to be fastened.

The above embodiments are given as illustrative examples and are not intended to impose any limitations on the invention. It will be readily appreciated that many deviations may be made from the specific embodiments disclosed in this specification without departing from the invention. Accordingly it is intended to cover all such modifications as within the scope of this invention.

What is claimed is:

1. A surgical fastener driver, comprising:
   a. a handle defining a cavity therein;
   b. a tube, in communication with the cavity and affixed to the handle, extending outwardly from the cavity to a seat, the seat being shaped so as to receive a surgical fastener therein;
   c. a piston, having an outward end, disposed within the tube and extending from the cavity to the seat, the piston having a retracted position, in which the outward end does not extend into the seat, and an extended position, in which the outward end extends into the seat;
   d. a trigger, integrated with the handle, having a first state in which the piston is held in the retracted position and a second state in which the piston is released so as to allow the piston to move to the extended position; and
   e. a driver, disposed within the cavity, that exerts outward force on the piston so as to drive the piston into the extended position when the trigger is in the second state;

wherein the piston has a first portion, having a first cross-section, and a second portion, having a second cross-section, the second cross-section being larger in area than the first cross-section;

and wherein the trigger includes a plate that defines a hole passing therethrough, the hole having a shape that allows the first portion to pass therethrough and prevents the second portion from passing therethrough when the plate is in a first position and that allows both the first portion and the second portion to pass therethrough when the plate is in a second position.

2. The surgical fastener driver of claim 1, wherein the tube tapers to a distal end adjacent to the seat.

3. The surgical fastener driver of claim 1, wherein the seat has a diameter substantially identical to an outer diameter of a fastener so as to frictionally engage the fastener therein.

4. The surgical fastener driver of claim 1, wherein the driver comprises a spring disposed within the cavity so as to exert force on the piston.

5. The surgical fastener driver of claim 4, wherein the spring is at rest when the piston is in the extended position and is compressed when the piston is in the retracted position.

6. The surgical fastener driver of claim 1, wherein the trigger includes a locking member that selectively holds the piston in the retracted position.

7. The surgical fastener driver of claim 1, wherein the trigger includes a second spring for maintaining the plate in the first position unless the plate is pushed into the second position by an operator.

8. The surgical fastener driver of claim 1, wherein the tube includes a first section, affixed to the handle, and a second section adjacent the seat, the second section deflecting at an angle from the first section, thereby facilitating surgical placement of a surgical fastener in a hard to reach area.

* * * * *